United States Patent
Dawson

Patent Number: 6,000,943
Date of Patent: Dec. 14, 1999

[54] TRAINING URINAL AND COMMODE

[76] Inventor: Loretta Dawson, 7923 Stillwell Rd., Cincinnati, Ohio 45237

[21] Appl. No.: 09/158,432

[22] Filed: Sep. 21, 1998

[51] Int. Cl.$^6$ .............................. A63B 69/00; A47K 11/00
[52] U.S. Cl. ........................... 434/247; 434/258; 4/144.1; 4/144.2; 4/301
[58] Field of Search ............................. 434/247; 4/144.1, 4/144.2, 300.3, 301, 305, 311, 471, 473, 476, 478, 479, 483, 485, 486

[56] References Cited

U.S. PATENT DOCUMENTS

| | | |
|---|---|---|
| D. 276,361 | 11/1984 | Hyman, Sr. . |
| D. 316,748 | 5/1991 | Penn . |
| D. 318,325 | 7/1991 | McKiney . |
| D. 379,407 | 5/1997 | Liu . |
| 706,566 | 8/1902 | Janes . |
| 2,592,040 | 4/1952 | La Hue . |
| 2,719,305 | 10/1955 | La Hue . |
| 2,769,982 | 11/1956 | Gossett . |
| 3,176,319 | 4/1965 | Mackey . |
| 3,327,324 | 6/1967 | Marsch . |
| 3,964,110 | 6/1976 | Kapit ............................................. 4/99 |
| 4,032,998 | 7/1977 | England . |
| 4,571,754 | 2/1986 | England . |
| 5,040,248 | 8/1991 | Kelly . |
| 5,044,020 | 9/1991 | Lewandowski et al. . |
| 5,148,553 | 9/1992 | Jermann . |
| 5,309,580 | 5/1994 | Amalsad et al. ............................. 4/483 |
| 5,388,279 | 2/1995 | Rasmussen . |
| 5,465,431 | 11/1995 | Wertz ....................................... 4/300.3 |
| 5,526,537 | 6/1996 | Conrad ........................................ 4/483 |
| 5,535,456 | 7/1996 | Chai ............................................ 4/449 |
| 5,822,804 | 10/1998 | Hauflaire ................................. 4/144.1 |

FOREIGN PATENT DOCUMENTS

| | | | |
|---|---|---|---|
| 90-4397 | 1/1924 | Rep. of Korea ............................ | 11/2 |

*Primary Examiner*—Robert A. Hafer
*Assistant Examiner*—Bena B Miller
*Attorney, Agent, or Firm*—Wood, Herron & Evans, L.L.P.

[57] ABSTRACT

A training commode for young girls or young boys is adaptable to be used also as a training urinal for young boys. The training commode can be used much the same way as a conventional training potty but, in addition and unlike conventional training potties, is readily converted to a training urinal to train young boys to urinate standing up. The height of the training urinal can be selectively adjusted to accommodate various sized young boys. The training commode is comprised of an outer structural shell having a base. Projecting upwardly from the center of the base is a telescopic stem. A bowl, which is mounted atop the stem, has a peripheral rim and a port for a collection reservoir which is in fluid communication with the bowl. Finally, a removable seat is selectively coupled to the rim of the bowl.

18 Claims, 2 Drawing Sheets

TRAINING URINAL AND COMMODE

FIELD OF THE INVENTION

The present invention generally relates to a training commode, and more specifically, to a training commode for young girls or young boys which is readily converted to a training urinal for training young boys.

BACKGROUND OF THE INVENTION

Potty training a young child is a normal part of the child rearing process. Using a conventional commode to potty train a young child is generally cumbersome and ineffective primarily because of the physical size of the conventional commode relative to a young child. Consequently, numerous training devices have been utilized in the past to assist the child during his or her potty training. For instance, training potties that provide for a toddler's seated use are well-known. Such training potties are suitable for both young boys and girls. However, potty training for young boys eventually includes training them to urinate while standing up so that they can successfully use a urinal commonly located in male bathrooms in restaurants, gas stations, stadiums, and the like. To this end, training urinals for the purpose of training young boys to urinate while standing are well-known.

Nevertheless, prior training devices suffer from various disadvantages. For example, most training devices are designed to function exclusively as either a training potty or a training urinal; that is, such training devices are seldom convertible front a training potty to a training urinal and vice versa. Accordingly, a young boy must use two separate training devices to successfully complete his potty training. What is needed is an easily adaptable training device that can readily convert from a training potty to a training urinal.

Another disadvantage of prior training urinals is the lack of height adjustability. Because a young boy may grow while still completing his potty training the height of the training urinal should be adjustable to accommodate the young boy's change of height. Furthermore, a training urinal without height adjustments may not be able to accommodate every potential user because some young boys may be too tall or too short to use a fixed-height training urinal. Prior training urinals have little or no height adjustment such that a growing young boy may outgrow the usefulness of the training urinal before his potty training is complete. Therefore, what is needed is a training urinal whose height can be readily and easily changed to accommodate young boys of varying heights.

SUMMARY OF THE INVENTION

In view of the foregoing disadvantages inherent in the known types of training devices now present in the prior art, the present invention provides a training commode adapted to be used as a training urinal for young boys. The training commode can be used much the same way as a conventions training potty for young boys or young girls but, in addition and unlike conventional training potties, is readily converted to a training urinal to train young boys to urinate standing up. The height of the training urinal can be selectively adjusted to accommodate various sized young boys or a single young boy who is growing during the potty training process.

In accordance with the principles of a presently preferred embodiment of the present invention, the training commode is comprised of an outer structural shell having a base. Projecting upwardly from the center of the base is a telescopic stem whose length is adjustable. A bowl, which s mounted atop the stem, has a peripheral rim extending around an upward portion of the bowl and a collection reservoir which is mounted within the bowl. Finally, a removable seat is selectively coupled to the rim of the bowl such that a young child, either boy or girl, can alternatively use the training commode like a conventional commode when sitting upon the seat on the rim, and as a training urinal for a young boy standing in front of and urinating into the bowl when the seat is removed from the rim. The height of the bowl is selectively adjustable via the telescoping stem depending upon the height of the boy.

In another aspect of the invention, the outer shell of the training commode includes an upright wall partially surrounding the base. The upright wall has a tote handle for carrying the training commode. Additionally, the bowl preferably includes a rear splash guard extending upwardly from the bowl, and the removable seat includes a forward splash guard positioned to minimize overspray from a user of the training commode. Finally, two armrests positioned for use by a user sitting on the training commode are preferably included.

A further feature of the invention includes a push button which is operatively connected to an electronic sound generator for generating a flushing sound. Once the user is finished using either the training commode or training urinal, the button can be pushed to generate a simulated flushing sound. Pushing the button helps train the user to flush after each use even though the training commode of the presently preferred embodiment is not connected to plumbing and cannot in fact flush.

By virtue of the invention, there is thus provided a training commode for both young boys and young girls which is readily convertible to a training urinal to train young boys to urinate standing up. The urinal height is easily adjusted to accommodate young boys of different heights. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate presently preferred embodiments of the invention and, together with the general description of the invention given above, and the detailed description of the embodiments given below, serve to explain the principles of the invention.

DETAILED DESCRIPTION OF THE PREFERRED EMBODIMENTS

Figures 1, 2:
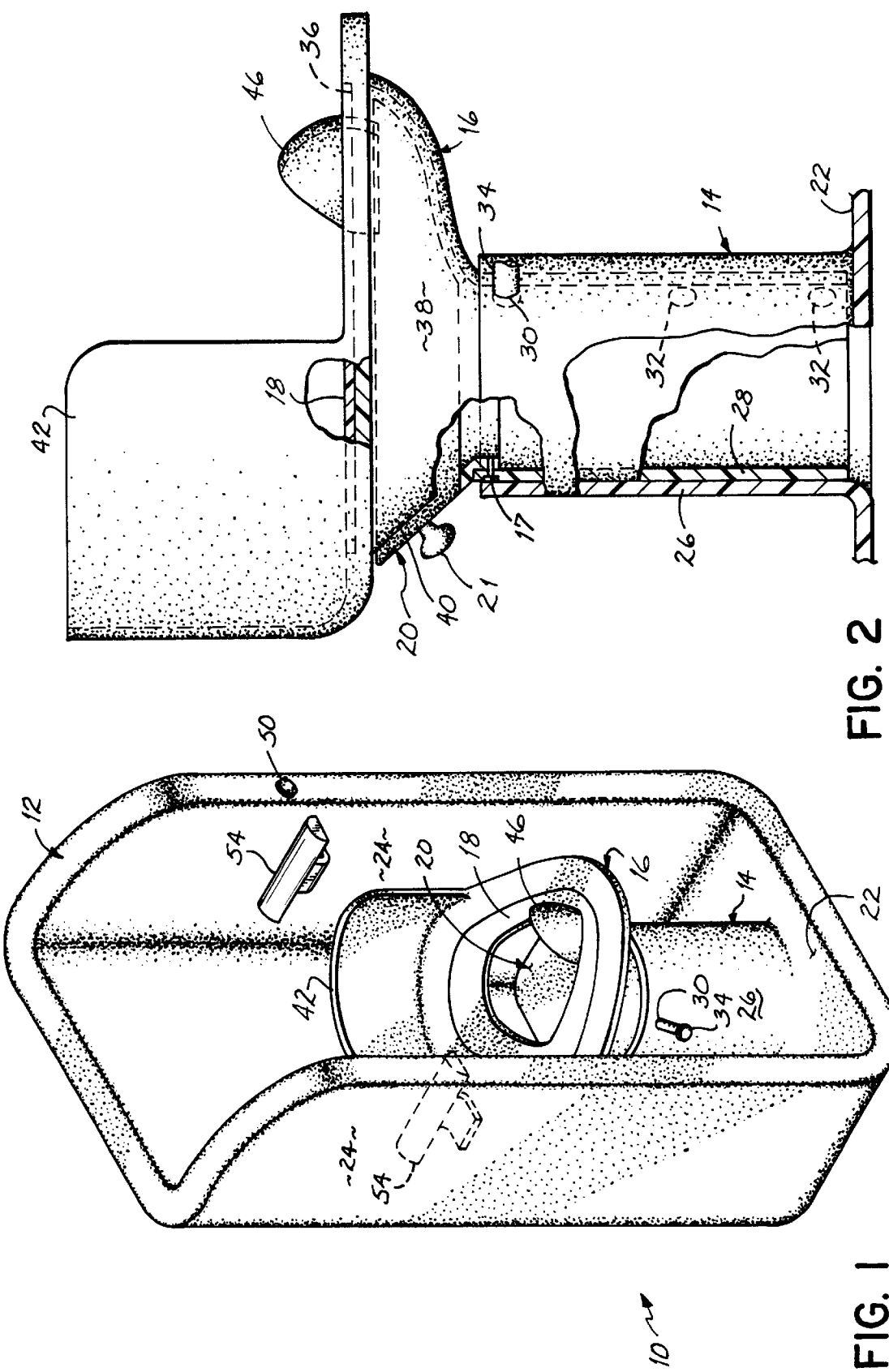
FIG. 1 is a perspective view of a training commode according to one embodiment of the invention.
FIG. 2 is a partial view of the training commode of FIG. 1; the structural shell being omitted for clarity.

With reference to FIG. 1 there s shown a training commode 10 in accordance with the principles of the present invention. The training commode 10 is comprised of an outer structural shell 12, a telescopic stem 14 whose height can be adjusted, a bowl 16 mounted atop of and secured to the stem via a bolt 17 (FIG. 2) or other fastening means, a removable seat 18 for use with the bowl, and a collection reservoir 20 contained within the bowl 16. Each component of the training commode 10 can be constructed from any suitable non-corrosive, structural material such as, but not limited to, rigid plastic or stainless steel. Furthermore, although the physical dimensions are not to be considered limitations on the present invention, it is contemplated that the training commode 10 will be sized to accommodate persons no larger than young children.

In accordance with the principles of presently preferred embodiments of the present invention, the outer structural shell 12 includes a base 22 and an upright wall 24 which partially surrounds the base. Projecting upwardly from base 22 is telescopic stem 14 where the height or length of the stem relative to the base is adjustable. Telescopic stem 14 comprises an external tube 26, which is affixed to or molded with base 22 and an internal tube 28, which can slide relative to the external tube. External tube 26 and internal tube 28 each include at least one throughhole 30, 32, respectively. Each throughhole 30, 32 is adapted to receive at least one pin 34 therethrough such that when the throughhole 30 of external tube 26 is aligned with throughhole 32 of internal tube 28, pin 34 can be inserted to fix the height of the telescopic stem 14. Advantageously, internal tube 28 has at least three throughholes 32 vertically aligned such that the height of the bowl 16 atop internal tube 28 of telescopic stem 14 can be selectively changed depending on the height of the boy.

Figure 3:
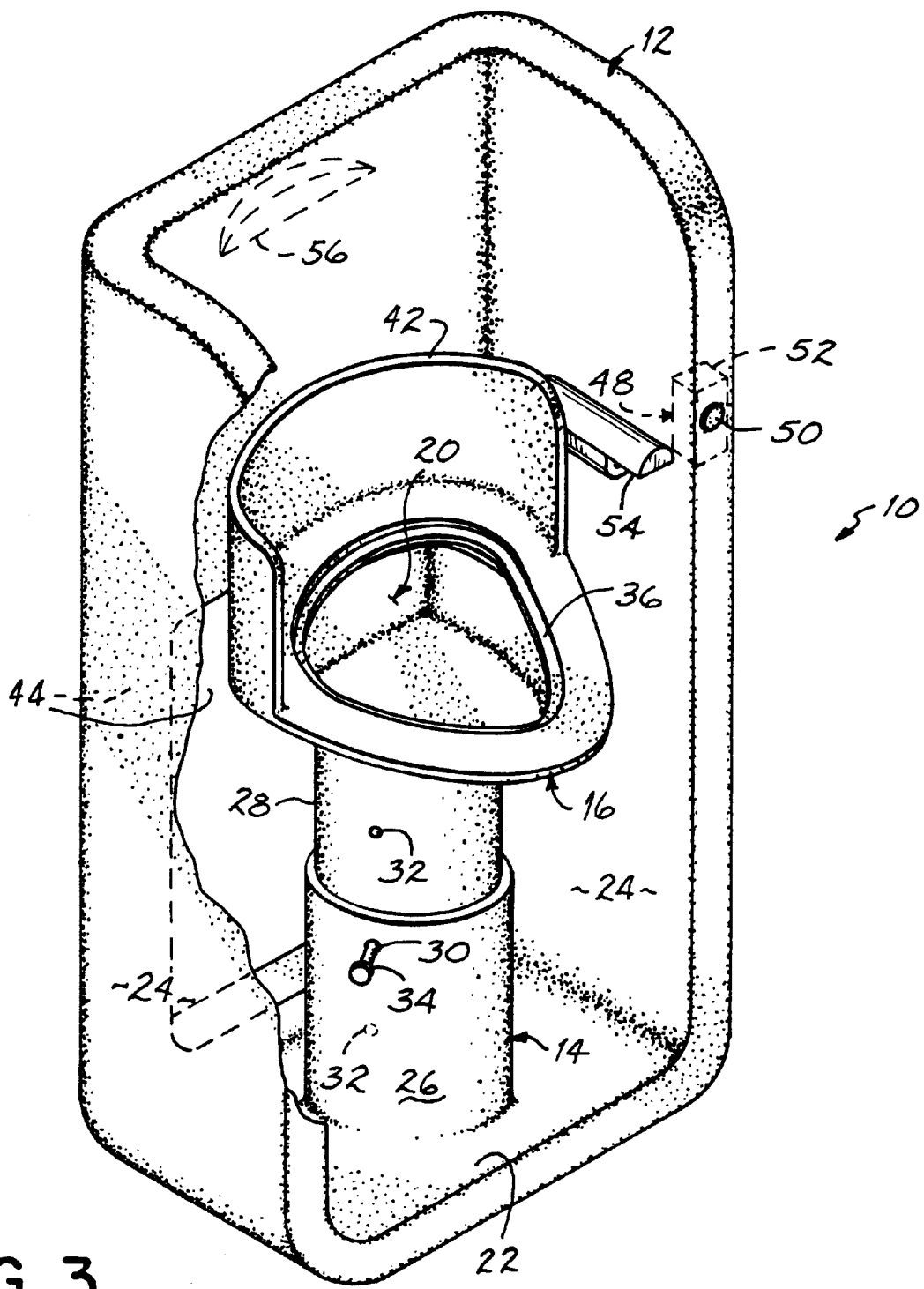
FIG. 3 is a perspective view, with partial cut-away, of the structural shell of FIG. 1 with the seat removed and the bowl height adjusted upwardly.

Mounted atop stem 14 is bowl 16 with a collection reservoir 20 selectively seated therein. As shown in FIG. 3, bowl 16 has a peripheral rim 36 extending around an upward portion 38 (FIG. 2) of bowl 16. Bowl 16 further includes a port 40 located at a rearward position on the bowl 16 and sized and configured to receive the collection reservoir 20 therein. Advantageously, bowl 14 includes a rear splash guard extending upwardly from the rear of the bowl. Rear splash guard 42 is shaped to catch and deflect urine overspray which may occur when a young boy is standing in front of and urinating into the training urinal.

Training commode 10 further includes the collection reservoir 20 which has a handle 21 and is removably mounted within the bowl 16 via the port 40. Advantageously, structural shell 12 includes an access opening 44 positioned and sized such that collection reservoir 20 can be removed therethrough, preferably when the seat 18 is lowered to the lowermost position via the telescopic stem 14. As such, a supervising adult can readily and conveniently remove the collection reservoir 20 via the handle 21 from the port 40 and through access opening 44 to empty its contents after the training commode 10 is used, clean and replace the collection reservoir 20 for subsequent use.

Training commode 10 also includes a removable seat 18 which is selectively coupled to rim 36 of bowl 16. Advantageously, seat 18 has a forward splash guard 46 positioned to minimize urine overspray from a user seated on the seat. With seat 18 positioned on rim 36, a young boy or young girl call use the training commode 10 like a conventional commode when sitting upon the seat mounted on the rim. Alternatively, with seat 18 removed from rim 36, a young boy can stand in front of and urinate into bowl 16.

In one embodiment of the present invention, the training commode 10 includes a device 48 (FIG. 3) for producing sound when the device is activated by a user of the training commode. Preferably, the device 48 is a push button 50 which is operatively connected to an electronic sound generator 52 capable of generating a flushing sound. A sound generator 52 suitable for use with this invention is readily known in the art, an example of which is disclosed in U.S. Pat. No. 5,535,456, incorporated by reference herein. Using the push button is considered a part of the potty training process. That is, once the user is finished using either the training commode or training urinal the button can be pushed to generate a simulated flushing sound. As such, the button helps train the user to flush after each use even though the training commode of the presently preferred embodiment is not connected to plumbing and cannot in fact flush in the conventional sense.

Another feature of the present invention, includes two armrests 54 which are positioned for use by a user sitting on the training commode. As illustrated in FIGS. 1 and 3, armrests 54 are mounted to and positioned on opposite sides of the upright wall 24. Additionally, upright wall 24 includes a tote handle 56 (FIG. 3) which is used to carry the training commode 10.

To use the training commode 10 like a conventional commode the removable seat 18 is placed onto rim 36 of bowl 16 with the collection reservoir 20 seated within the bowl 16. To best accommodate a seated child, the telescopic stem 14 and therefore the bowl 16 is lowered to its lowest height. At this lowered bowl height, a young child, male or female, can comfortably use the training commode 10 in much the same way as the child will eventually use a conventional commode.

To train young boys to use a urinal, the training commode 10 is readily converted to function as a training urinal. To this end, seat 18 is removed from rim 36 of bowl 16. Additionally, because the training urinal will be used by young boys in a standing position, the height of the telescopic stem 14 and therefore the bowl 16 is adjusted upwardly to simulate the use of a conventional urinal. Whether used as training commode or training urinal, pushing button 50 after each use to simulate a flushing sound helps the young child establish the habit of flushing after each use.

While the present invention has been illustrated by a description of various presently preferred embodiments and while these embodiments have been described in considerable detail to describe the best mode of practicing the invention, the description herein does not restrict or in any way limit the scope of the appended claims to such detail. Additional advantages and modifications within the spirit and scope of the invention will readily appear to those skilled in the art. The invention itself should only be defined by the appended claims and equivalents thereof.

I claim:

1. A training commode comprising:
    an outer structural shell having a base;
    a telescopic stem projecting upwardly from said base, a height of said stem relative to said base being adjustable;
    a bowl mounted atop said stem, a peripheral rim extending around an upward portion of the bowl; wherein the bowl is independent from the shell,
    a selectively removable waste collection reservoir in fluid communication with said bowl; and
    a selectively removable seat coupled to said rim of said bowl such that a young child can alternatively use the training commode by sitting upon said seat on said rim, and as a training urinal for a young boy standing in front of and urinating into said bowl when said seat is removed from said rim, the height of said bowl being selectively adjusted via said telescoping stem depending upon the height of the boy.

2. The training commode of claim 1, wherein said telescopic stem includes an external tube and an internal tube, where said external tube is affixed to said base and said internal tube can slide relative to said external tube;

said external tube and said internal tube each include at least one throughhole adapted to receive at least one pin therethrough such that said height of said bowl atop said internal tube can be selectively changed.

3. The training commode of claim 1, wherein said bowl further includes a rear splash guard extending upwardly from said bowl.

4. The training commode of claim 1, wherein said removable seat further includes a forward splash guard projecting upwardly above said removable seat and positioned to minimize urine overspray from a user seated on said seat.

5. The training commode of claim 1, wherein said structural shell includes an access opening positioned and sized such that said waste collection reservoir can be removed therethrough and said bowl includes a port into which the collection reservoir is selectively mounted.

6. The training commode of claim 1, further comprising:

a device for producing sound when said device is activated by a user of the training commode.

7. The training commode of claim 6, wherein said device is a push button operatively connected to an electronic sound generator for generating a flushing sound.

8. A training commode comprising:

an outer structural shell having a base and an upright wall partially surrounding said base, said upright wall having two armrests positioned for use by a user sitting on the training commode, said upright wall also having a tote handle for carrying the training commode;

a telescopic stem projecting upwardly from said base, a height of said stem relative to said base being adjustable;

a bowl mounted atop said stem, a peripheral rim extending around an upward portion of the bowl;

a selectively removable waste collection reservoir in fluid communication with said bowl; and a selectively removable seat coupled to said rim of said bowl such that a young child can alternatively use the training commode by sitting upon said seat on said rim, and as a training urinal for a young boy standing in front of and urinating into said bowl when said seat is removed from said rim, the height of said bowl being selectively adjusted via said telescoping stem depending upon the height of the boy.

9. A stand alone training urinal comprising:

an outer structural shell having a floor supported base;

a telescopic stem projecting upwardly from the center of said base, wherein a height of said stem relative to said base being adjustable;

a bowl mounted atop said stem, a peripheral rim extending around an upward portion of the bowl; wherein the bowl is independent from the shell, and a selectively removable waste collection reservoir in fluid communication with said bowl;

wherein a young boy standing in front of the training urinal urinates into said bowl for collection by said reservoir and said height of said bowl can be selectively adjusted via said telescoping stem depending upon the height of the boy.

10. The training commode of claim 9, wherein said telescopic stem includes an external tube and an internal tube, where said external tube is affixed to said base and said internal tube can slide relative to said external tube;

said external tube and said internal tube each include at least one throughhole adapted to receive at least one pin therethrough such that said height of said bowl atop said internal tube can be selectively changed.

11. The training urinal of claim 9, wherein said bowl further includes a rear splash guard extending upwardly from said bowl.

12. The training urinal of claim 9, wherein said structural shell includes an access opening positioned and sized such that said waste collection reservoir can be removed therethrough and said bowl includes a port into which the collection reservoir is selectively mounted.

13. The training urinal of claim 9, further comprising;

a removable seat selectively coupled to said peripheral rim and said removable seat rests upon said rim of said bowl converting the training urinal into a training commode so that a young child can sit upon said seat.

14. The training urinal of claim 13, wherein said removable seat further includes a forward splash guard projecting upwardly above said removable seat and positioned to minimize urine overspray from a user sitting on said removable seat.

15. The training urinal of claim 9, further comprising:

a device for producing sound when said device is activated by a user of the training urinal.

16. The training urinal of claim 15, wherein said device is a push button operatively connected to an electronic sound generator for generating a flushing sound.

17. A training commode adapted to be used as a training urinal for young boys comprising:

an outer structural shell having a base and an upright wall partially surrounding said base, said upright wall having a tote handle for carrying the training commode;

a telescopic stem projecting upwardly from the center of said base;

a bowl mounted atop said stem and having a port therein, a peripheral rim extending around an upward portion of said bowl, said bowl including a rear splash guard extending upwardly therefrom; and a height of said bowl being adjustable via said telescopic stem; wherein the bowl is independent from the shell, a selectively removable waste collection reservoir mounted in said bowl via said port and being in fluid communication with said bowl, where said structural shell includes an access opening positioned and sized such that said collection reservoir can be removed therethrough;

a removable seat having a forward splash guard projecting upwardly above said removable seat and positioned to minimize urine overspray from a user of the training commode, said seat rests coupled to said rim of said bowl such that a young child can alternatively use the training commode by sitting upon said seat on said rim, and as a training urinal for a young boy standing in front of and urinating into said bowl when said seat is removed from said rim, the height of said bowl being selectively adjusted via said telescoping stem depending upon the height of the boy; and two armrests positioned for use by a user sitting on the training commode.

18. The training commode of claim 17, further comprising:

a device for producing sound when said device is activated by a user of the training commode.

* * * * *